(12) United States Patent
Bonn

(10) Patent No.: US 8,131,339 B2
(45) Date of Patent: Mar. 6, 2012

(54) SYSTEM AND METHOD FOR FIELD ABLATION PREDICTION

(75) Inventor: Kenlyn S. Bonn, Boulder, CO (US)

(73) Assignee: Vivant Medical, Inc., Boulder, CO (US)

( * ) Notice: Subject to any disclaimer, the term of this patent is extended or adjusted under 35 U.S.C. 154(b) by 590 days.

(21) Appl. No.: 12/274,440

(22) Filed: Nov. 20, 2008

(65) Prior Publication Data

US 2009/0138004 A1     May 28, 2009

Related U.S. Application Data

(60) Provisional application No. 60/990,373, filed on Nov. 27, 2007.

(51) Int. Cl.
*A61B 5/05* (2006.01)
(52) U.S. Cl. .......................... 600/411; 600/410; 606/34
(58) Field of Classification Search ............... 606/34, 606/33; 600/410, 411
See application file for complete search history.

(56) References Cited

U.S. PATENT DOCUMENTS

| | | | |
|---|---|---|---|
| 3,631,363 A | 12/1971 | Miller | |
| 4,397,313 A | 8/1983 | Vaguine | |
| 4,462,412 A | 7/1984 | Turner | |
| 4,572,190 A | 2/1986 | Azam et al. | |
| 4,798,215 A | 1/1989 | Turner | |
| 5,097,844 A | 3/1992 | Turner | |
| 5,417,210 A | 5/1995 | Funda et al. | |

(Continued)

FOREIGN PATENT DOCUMENTS

DE      390937      3/1924

(Continued)

OTHER PUBLICATIONS

U.S. Appl. No. 08/483,742, filed Jun. 7, 1995.

(Continued)

*Primary Examiner* — Laura Bouchelle

(57) ABSTRACT

A system for determining field of ablation is disclosed. The system includes a power source configured to generate electromagnetic energy and an energy applicator coupled to the power source. The energy applicator is configured to be inserted into tissue and to provide electromagnetic energy to a target volume. The system also includes an imaging apparatus configured to generate a uniform magnetic field and at least one variable magnetic field around the tissue. The imaging apparatus obtains an image of a field of ablation within the target volume in response to a trace RF pulse supplied by the power source through the energy applicator to the target volume simultaneously with an excitation RF pulse generated by the imaging apparatus and the at least one variable magnetic field.

20 Claims, 3 Drawing Sheets

U.S. PATENT DOCUMENTS

| | | | |
|---|---|---|---|
| 5,571,147 | A | 11/1996 | Sluijter et al. |
| 6,031,375 | A | 2/2000 | Atalar et al. |
| 6,241,725 | B1 | 6/2001 | Cosman |
| 6,246,912 | B1 | 6/2001 | Sluijter et al. |
| 6,277,083 | B1 | 8/2001 | Eggers et al. |
| 6,355,033 | B1 | 3/2002 | Moorman et al. |
| 6,375,606 | B1 | 4/2002 | Garibaldi et al. |
| 6,451,015 | B1 | 9/2002 | Rittman, III et al. |
| 6,471,659 | B2 | 10/2002 | Eggers et al. |
| 6,478,793 | B1* | 11/2002 | Cosman et al. ............. 606/34 |
| 6,506,189 | B1 | 1/2003 | Rittman, III et al. |
| 6,530,922 | B2 | 3/2003 | Cosman et al. |
| 6,575,969 | B1 | 6/2003 | Rittman, III et al. |
| 6,582,726 | B1 | 6/2003 | Geysen et al. |
| 6,603,994 | B2 | 8/2003 | Wallace et al. |
| 6,706,040 | B2 | 3/2004 | Mahon et al. |
| 6,725,080 | B2 | 4/2004 | Melkent et al. |
| 6,881,214 | B2 | 4/2005 | Cosman et al. |
| 7,008,421 | B2 | 3/2006 | Daniel et al. |
| 7,160,292 | B2 | 1/2007 | Moorman et al. |
| 7,194,297 | B2 | 3/2007 | Talpade et al. |
| 7,207,985 | B2 | 4/2007 | Duong et al. |
| 7,223,264 | B2 | 5/2007 | Daniel et al. |
| 7,341,586 | B2 | 3/2008 | Daniel et al. |
| 7,439,736 | B2 | 10/2008 | Meaney et al. |
| 7,467,015 | B2 | 12/2008 | Van der Weide |
| 7,480,533 | B2 | 1/2009 | Cosman et al. |
| 7,565,207 | B2 | 7/2009 | Turner et al. |
| 2002/0022836 | A1 | 2/2002 | Goble et al. |
| 2004/0039429 | A1 | 2/2004 | Daniel et al. |
| 2004/0097805 | A1 | 5/2004 | Verard et al. |
| 2004/0242992 | A1* | 12/2004 | Hareyama .............. 600/411 |
| 2007/0161997 | A1 | 7/2007 | Thramann et al. |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 159 926 | 5/2001 |
| EP | 1 278 007 | 1/2003 |
| EP | 1 810 627 | 7/2007 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO 96/34571 | 11/1996 |
| WO | WO97/41924 | 11/1997 |
| WO | WO97/43971 | 11/1997 |
| WO | WO 99/04710 | 2/1999 |
| WO | WO 99/58065 | 11/1999 |
| WO | WO00/48672 | 8/2000 |
| WO | WO00/51513 | 9/2000 |
| WO | WO01/01847 | 1/2001 |
| WO | WO01/74252 | 10/2001 |
| WO | WO02/45790 | 6/2002 |
| WO | WO02/061880 | 8/2002 |
| WO | WO2004/112628 | 12/2004 |
| WO | WO2005/016119 | 2/2005 |
| WO | WO 2006/105121 | 10/2006 |

OTHER PUBLICATIONS

U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.

U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,150, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.

Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Radiofrequency Lesion Generation and its Effect on Tissue Impedance", Applied Neurophysiology, 51:230-242, 1988.
Cosman et al., Theoretical Aspects of "Radiofrequency Lesions in the Dorsal Root Entry Zone" Neurosurgery 15:(1984), pp. 945-950.
Cosman et al., "Methods of Making Nervous System Lesions" In William RH, Rengachary SS (eds): Neurosurgery, New York: McGraw•Hill, vol. 111, (1984), pp. 2490-2499.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure™ Vessel Sealing System for Peri-Hilar Vessels in Laparoscopic Nephrectomy" Sales/Product Literature 2000.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General, Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, pp. 205-210.

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics FIGO World Congress 2000, Washington, DC.

MDTECH product literature (Mar. 2000) I'D Wire: product description, 1 page.

MDTECH product literature (Dec. 1999) "FlexStrand": product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized..." Journal of Applied Sciences-Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Oapril 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.

Rothenberg et al., "Use of the LigaSure™ Vessel Sealing System in Minimally Invasive Surgery in Children" Int'l Pediatric Endosurgery Group (I PEG) 2000.

Sayfan et al., "Sutureless Closed Hemorrhoidectomy: A New Technique" Annals of Surgery, vol. 234, No. 1, Jul. 2001, pp. 21-24.

Sengupta et al., "Use of a Computer-Controlled Bipolar Diathermy System in Radical Prostatectomies and Other Open Urological Surgery" ANZ Journal of Surgery (2001) 71.9 pp. 538-540.

Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Long-term Results in 117 Patients", Radiology, vol. 221, pp. 159-166.

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.

Stuart W. Young, Nuclear Magnetic Resonance Imaging—Basic Principles, Raven Press, New York, 1984.

Sugita et al., "Bipolar Coagulator with Automatic Thermocontrol" J. Neurosurg., vol. 41, Dec. 1944, pp. 777-779.

Sylvain Labonte et al., "Monopole Antennas for Microwave Catheter Ablation", IEEE Trans. on Microwave Theory and Techniques, vol. 44, No. 10, pp. 1832-1840, Oct. 1995.

T. Matsukawa et al., "Percutaneous Microwave Coagulation Therapy in Liver Tumors", Acta Radiologica, vol. 38, pp. 410-415, 1997.

T. Seki et al., (1994) "Ultrasonically Guided Percutaneous Microwave Coagulation Therapy for Small Hepatocellular Carcinoma," Cancer 74(3):817-825.

S. Humphries Jr. et al., "Finite-Element Codes to Model Electrical Heating and Non-Llnear Thermal Transport in Biological Media", Proc. ASME HTD-355, 131 (1997).

Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.

Urrutia et al., (1988). "Retractable-Barb Needle for Breast Lesion Localization: Use in 60 Cases," Radiology 169(3):845-847.

Valleylab Brochure, "Valleylab Electroshield Monitoring System" 2 pages, Nov. 1995.

ValleyLab Brochure, "Electosurgery: A Historical Overview", Innovations in Electrosurgery, 1999.

Vallfors et al., "Automatically Controlled Bipolar Electrocoagulation-'COA-COMP'" Neurosurgical Review 7:2-3 (1984) pp. 187-190.

W. Scott Helton, "LigaSure™ Vessel Sealing System: Revolutionary Hemostasis Product for General Surgery" Sales/Product Literature 1999.

Wald et al., "Accidental Burns", JAMA, Aug. 16, 1971, vol. 217, No. 7, pp. 916-921.

Walt Boyles, "Instrumentation Reference Book", 2002, Butterworth-Heinemann, pp. 262-264.

European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.

European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report EP08169973 dated Apr. 6, 2009.
Schwarzmaier H-J et al: "Magnetic Resonance Imaging of Microwave Induced Tissue Heating" Magnetic Resonance in Medicine, Academic Press, Duluth, MN, US, vol. 33, No. 5, May 1, 1995, pp. 729-731, XP000620374 ISSN: 0740-3194.
Esterline Product Literature, "Light Key: Visualize a Virtual Keyboard One With No Moving Parts", Nov. 1, 2003; 4 pages.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.

* cited by examiner

SYSTEM AND METHOD FOR FIELD ABLATION PREDICTION

CROSS-REFERENCE TO RELATED APPLICATIONS

This application claims the benefit of priority to U.S. Provisional Application Ser. No. 60/990,373 entitled "SYSTEM AND METHOD FOR FIELD ABLATION PREDICTION" filed Nov. 27, 2007 by Kenlyn Bonn, which is incorporated by reference herein.

BACKGROUND

1. Technical Field

The present disclosure relates to electrosurgical and microwave ablation apparatuses, systems and methods. More particularly, the present disclosure is directed to a system and method for determining the field of ablation prior to a tissue ablation procedure utilizing electrosurgical electrodes and/or microwave antennas and imaging means.

2. Background of Related Art

Energy-based tissue treatment is well known in the art. Various types of energy (e.g., electrical, ultrasonic, microwave, cryogenic, heat, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator. In the case of tissue ablation, high radio frequency electrical current is applied to a targeted tissue site to create an ablation volume.

Microwave ablation also creates lesions by desiccating target tissue volume. Microwave energy is also a type of electromagnetic radio frequency energy similar to the type used in electrosurgical ablation but at a higher frequency. Prior to performing ablation procedures it is desirable to estimate the resulting volume of the lesion.

The resulting ablation volume may then be observed and various ablation metrics may be measured and recorded. Conventional methods of obtaining ablation metrics include recording the small diameter, large diameter, and height of the ablated tissue to calculate the volume. Typically, these three parameters are input for the equation for ellipsoidal volume to calculate an approximate ablation volume. Conventional methods such as this often provide inexact measurements, inconsistent recordings, as well as inaccurate reporting of achieved volumes. Further, conventional methods of volumetric calculation lack evaluative tools such as determining the effect of adjacent structures on the ablation volume, qualifying the completeness of the ablation volume, predicting specific volumes and/or shapes based on a given energy applicator configuration.

SUMMARY

The present disclosure relates to a system and method for determining the field of ablation using energy deposition antennas (e.g., electrosurgical electrodes, microwave probes, etc.). The system includes a magnetic or electron imaging apparatus (e.g., MRI) which interfaces with an ablation energy power source. The power source is also coupled to one or more energy deposition antennas. During operation, the imaging apparatus signals the power source to apply a tracer pulse sufficient to modify alignment of atoms thereby producing a simulated ablation field. The imaging apparatus thereafter proceeds with measuring the alignment of the atoms and produces an image illustrative of the simulated ablation field.

According to one aspect of the present disclosure, a system for determining a field of ablation is disclosed. The system includes a power source configured to generate electromagnetic energy and an energy applicator coupled to the power source. The energy applicator is configured to be inserted into tissue and to provide electromagnetic energy to a target volume. The system also includes an imaging apparatus configured to generate a uniform magnetic field and one or more variable magnetic fields around the tissue. The imaging apparatus obtains an image of a field of ablation within the target volume in response to a trace RF pulse supplied by the power source through the energy applicator to the target volume simultaneously with an excitation RF pulse generated by the imaging apparatus and the variable magnetic fields.

A method for determining a field of ablation is also contemplated by the present disclosure. The method includes the step of providing a power source configured to generate electromagnetic energy and an energy applicator coupled to the power source. The energy applicator is configured to be inserted into tissue and to provide electromagnetic energy to a target volume. The method also includes the steps of placing tissue into an imaging apparatus and generating a uniform magnetic field and one or more variable magnetic field around the tissue, supplying simultaneously a trace RF pulse through the energy applicator to the target volume and an excitation RF pulse with the variable magnetic fields and obtaining an image of a field of ablation within the target volume in response to the trace RF pulse supplied by the power source.

According to another aspect of the present disclosure, a system for determining a field of ablation is disclosed. The system includes a power source configured to generate electromagnetic energy and an energy applicator coupled to the power source. The energy applicator is configured to be inserted into tissue and to provide electromagnetic energy to a target volume. The system also includes an MRI system configured to generate a uniform magnetic field and one or more variable magnetic fields around the tissue. The MRI system obtains an image of a field of ablation within the target volume in response to a trace RF pulse supplied by the power source through the energy applicator to the target volume simultaneously with an excitation RF pulse generated by the MRI system and the variable magnetic fields. The system further includes an interface controller coupled to the power source and the MRI system and configured to synchronize operation thereof to provide for simultaneous application of the trace RF pulse and the excitation RF pulse.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The present disclosure provides for a system and method for determining a field of ablation created by applying electromagnetic energy such as radiofrequency ("RF") and microwave energy. The system includes a magnetic and/or electron imaging apparatus that is synchronously interfaced with electromagnetic energy applicators (e.g., high RF electrodes and microwave antennas). The imaging apparatus obtains images of target tissue by initially pairing opposing spin atoms in a magnetic field. The system then generates an image of an ablation field prior to application of therapeutic energy by manipulating the magnetic field of the imaging apparatus through the applicator. In particular, a tracer pulse is transmitted through the energy applicator which misalignes the unpaired atoms. The energy released by the misaligned atoms is then recorded by the imaging apparatus as potential field of ablation.

Figure 1:
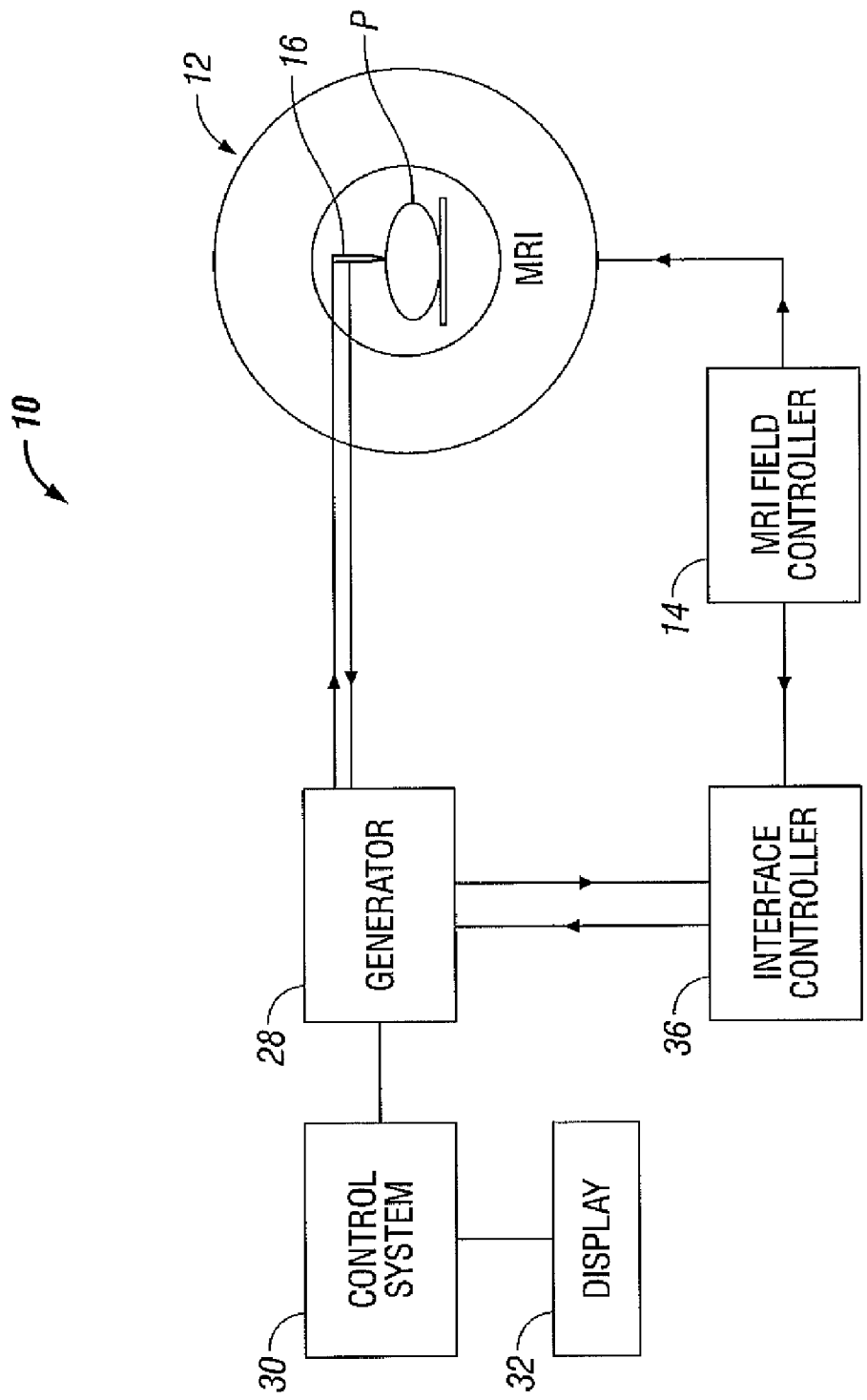
FIG. 1 shows an embodiment of an electrosurgical system for determining a field of tissue ablation according to the present disclosure.

Referring to FIG. 1, a system 10 for determining a field of ablation is shown. The system 10 includes an imaging apparatus, such as a magnetic resonance imaging ("MRI") system 12 suitable for obtaining images of a tissue sample or a patient "P" placed therein. Those skilled in the art will appreciate that the imaging apparatus 12 may be of either "open" or "closed" configuration providing varying degrees of access to the patient.

The MRI system 12 utilizes a static magnetic field, an RF transmitter and receiver, and a plurality of orthogonal, controllable magnetic gradients. More specifically, MRI system 12 generates a powerful, uniform magnetic field into which the patient "P" is placed. When subjected to the magnetic field, the spins of atomic nuclei, such as those of hydrogen nuclei in water and lipids, which have a resulting non-zero spin, arrange in a particular manner. In particular, nuclei of hydrogen atoms have a so-called "simple half spin" and therefore align either in parallel or unparallel to the magnetic field. The majority of atoms have a pairing partner with an opposing spin and are therefore canceled out. Some of the hydrogen atoms are not paired and are used as image components by passing an RF pulse through the object.

In order to obtain a desired image of the subject, orthogonal magnetic gradients and an excitation RF pulse are applied that provide a desired slice of the area. The MRI system 12 is coupled to an MRI field controller 14 that controls the gradient magnets (not explicitly shown) to generate the localized magnetic fields. Concurrently with the gradient magnets, the excitation RF pulse of defined bandwidth is applied by the RF. The RF pulse causes unpaired atoms to precess in a different direction. Once the RF pulse is terminated, the misaligned hydrogen atoms return to their original orientation, releasing a burst of energy recorded by the RF receiver. The recorded energy is then analyzed to obtain an image of the target tissue.

Each specific tissue type has a designated frequency, the Lamour frequency, at which the change in spin occurs under a predetermined magnetic field. Tumors or abnormal tissue have different Lamour frequencies than normal, healthy tissue. This difference in Lamour frequency allows for visual detection of the tumor since the different spin orientation produces areas of different contrast in the image (e.g., tumors and abnormal tissue have a different shade and/or color than normal tissue).

Figure 2:
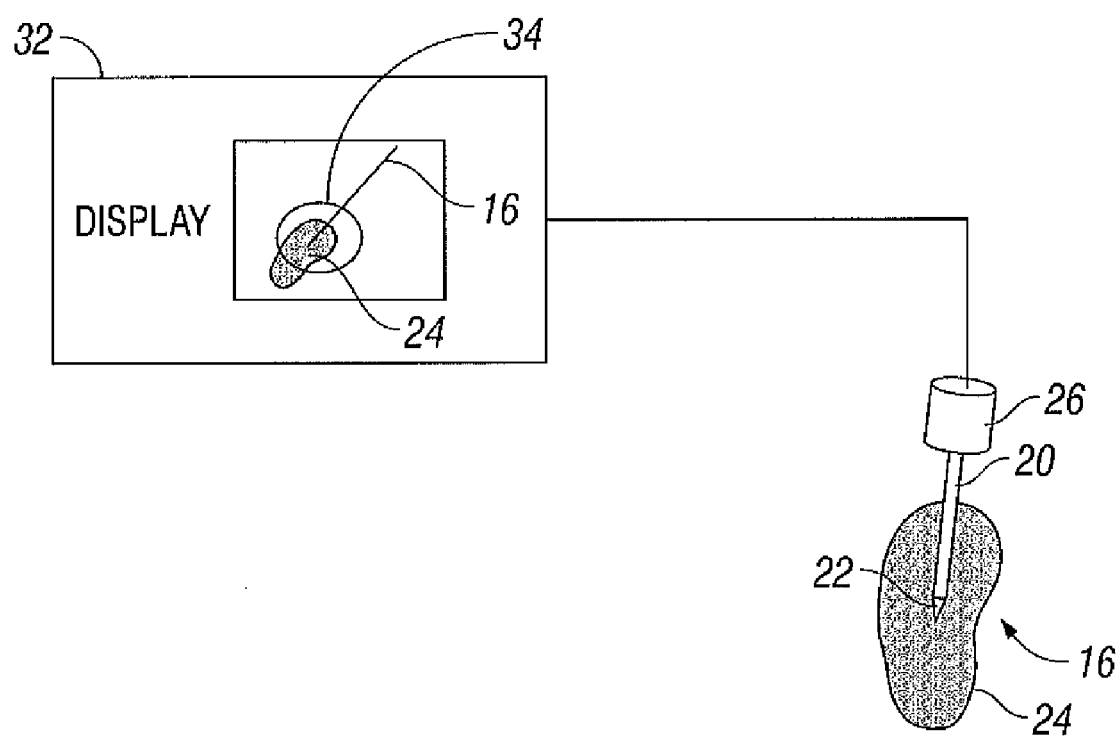
FIG. 2 shows an embodiment of an ablation applicator according to the present disclosure.

The system 10 also includes an ablation applicator 16, which may be any type of applicator suitable for depositing electromagnetic energy (e.g., high frequency RF energy, microwave, etc.) into the tissue. In one embodiment, the applicator 16 may be an electrosurgical electrode or a microwave antenna as shown in more detail in FIG. 2. The applicator 16 may include an insulated shaft 20 and an electrically conductive tip 22. In one embodiment, wherein microwave energy is being applied, the applicator 16 may include a non-conductive tip.

Applicator 16 is configured to be placed in the body of a patient (not explicitly shown in FIG. 2) so that the tip 22 is near a target volume 24, such as a cancerous tumor or other tissue structure within the patient "P." A hub or junction connector element illustrated schematically by 26 may be any suitable type of connection device, such as jacks, hoses, ports, etc., that connect the applicator 16 to a power source (e.g., generator 28) or other suitable surgical equipment (e.g., a coolant supply). The applicator 16 (e.g., components thereof) may be formed from MRI compatible materials, such as safe magnetic resonance materials (e.g., non-conductive and non-magnetic) and conditional magnetic resonance materials (e.g., demonstrated to pose no known hazards in a specified MRI environment with specified conditions of use) as defined by American Society for Testing and Materials (ASTM) International, Designation: F 2503-05. Even trace amounts of magnetic material may result in artificial imaging artifacts, which may limit the visibility and precise orientation of the applicator 16 inside the patient.

Referring back to FIG. 1, in one embodiment, the generator 28 may be a microwave generator having a magnetron for generating microwave energy. The microwave energy may be transmitted to the applicator 16 through a coaxial cable having an inner conductor and an outer conductor separated by an insulating member. In another embodiment, the generator 28 may be an electrosurgical generator having an RF output stage for generating high frequency AC energy. The generator 28 may provide electrosurgical energy suitable for performing monopolar and bipolar electrosurgical procedures, including tissue ablation procedures. The generator 28 may include a plurality of outputs for interfacing with various electrosurgical instruments (e.g., a monopolar active electrode, return electrode, bipolar electrosurgical forceps, footswitch, etc.). Further, the generator 28 may include suitable electronic circuitry configured for generating radio frequency power specifically suited for various electrosurgical modes (e.g., cutting, blending, division, etc.) and procedures (e.g., monopolar, bipolar, vessel sealing, tissue ablation).

The system 10 also includes a control system 30 coupled to the generator 28, which may be a computer, a microprocessor, or an electromechanical device configured to provide input parameters to the generator 28, such as power, current, voltage, energy, time, impedance, etc. The control system 30 modulates, moderates, or otherwise monitors output response of the generator 28 based on one or more of these parameters.

In one embodiment, the control system 30 stores various operating parameters of the applicator 10 such as energy deposition characteristics, magnetic field characteristics, etc. This allows the control system 30 to adjust the operating parameters of the generator 28 and the MRI field controller 14.

The control system 30 is also coupled to the MRI system 12 and is configured to receive image data therefrom. The data may be stored in the control system 30 and be represented as an array of raw data, slices, reconstructed slices, three-dimensional renderings, "slice and dice" three-dimensional or two-dimensional renderings, contoured or segmented anatomical structures, color rendered, differentiated structures, both pathological and normal so that the surgeon may substantially visualize the anatomy and pathology of the patient prior to, during, or after the procedure.

The control system 30 is also coupled to a display 32 for outputting image data, such as a field of ablation 34 (FIG. 2) of the applicator 16 with respect to the target volume 24. The field of ablation 34 is obtained by the MRI system 12 as discussed in more detail below. Display 32 may also be configured to show a preplanned path of the applicator 16 in a particular slice or reconstructed slice plane of volumetric rendering in a three-dimensional aspect (not explicitly shown), and also configured to show isotherm surfaces or intersected surfaces or isotherm lines (not explicitly shown), which might represent a preplan or a calculation of the ablation volume around the tip of the electrode. Display 32 may also be configured to show a view, slice, or reconstructed slice, and within it a preplanned or actual plan or post-thermosurgery path representing the approach of the applicator 16 into the patient's anatomy to achieve a target volume that might be seen on that image slice such as for example a tumor.

The system 10 also includes an interface controller 36 that is coupled to the generator 28 and the MRI field controller 14. The interface controller 36 synchronizes the operation of the generator 28 and the MRI field controller 14 to obtain field of ablation. The operation of the interface controller 36 and other components of the system 10 is described in more detail with reference to FIG. 3.

Figure 3:
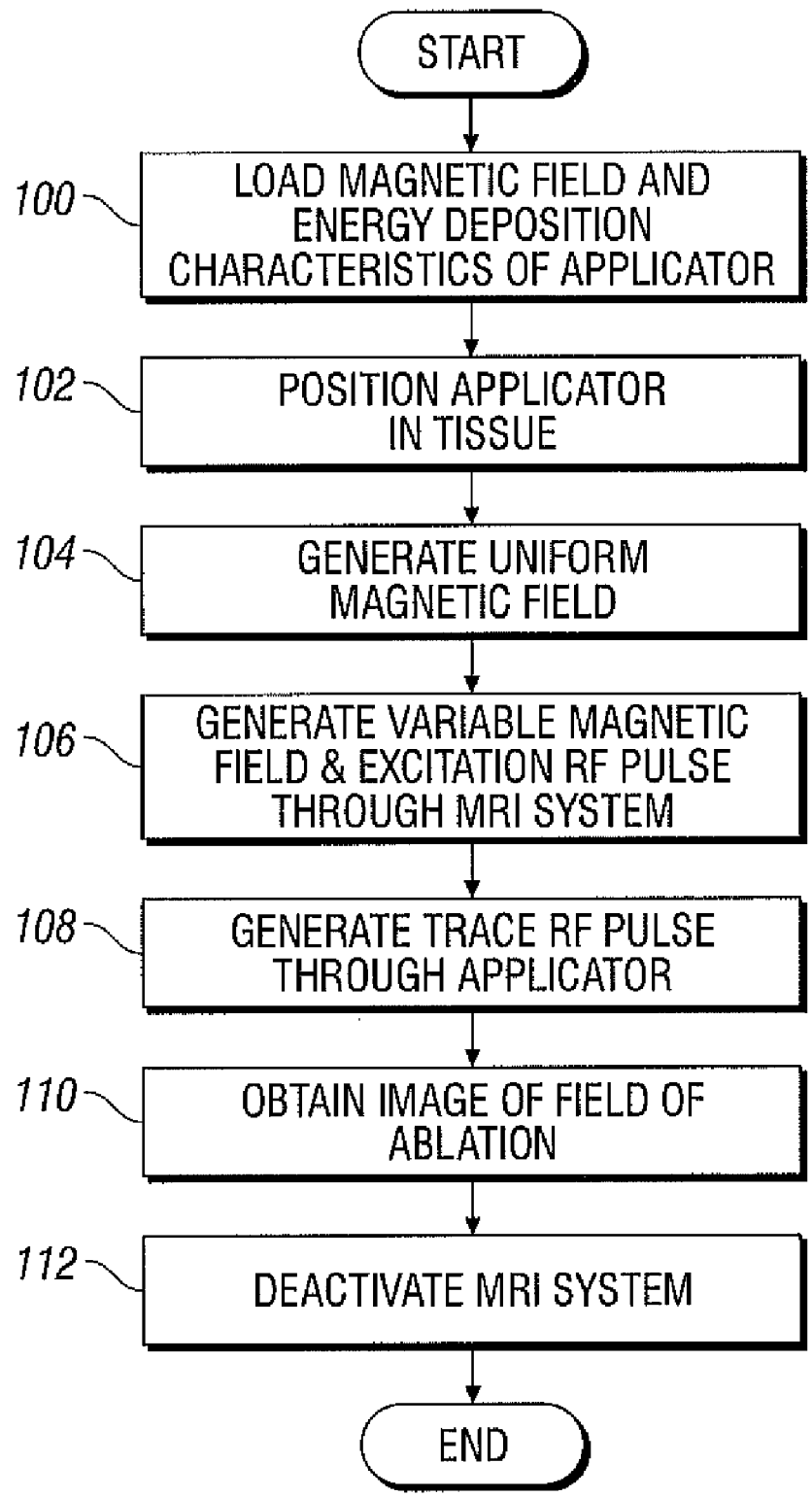
FIG. 3 illustrates a method for determining a field of tissue ablation according to the present disclosure.

FIG. 3 illustrates a method for determining the field of ablation 34 using the system 10 according to one embodiment of the disclosure. In step 100, the user sets up the generator 28 and the MRI system 12. The magnetic field and energy deposition characteristics of the applicator 16 are loaded into the control system 30. Each applicator 16 has unique characteristics based on the components and materials thereof. By inputting the characteristics of the applicator 16 into the control system 30, the magnetic field developed by the applicator 16 can be more predictable. Since the MRI utilizes the Lamour frequency to generate different contrast areas on the resulting image, providing predictable magnetic field of the applicator 16 allows for utilization of the Lamour frequency of the tissue being examined to predict the field of ablation 34.

In step 102, the applicator 16 is inserted into the tissue volume until the applicator 16 is positioned at the target volume 24. This may be accomplished by using various imaging means having either real-time or previously recorded data to guide the applicator 16 to the site. The MRI system 12 may be used to provide for pre-recorded image data. In one embodiment CT scans may also be utilized. Further, ultrasound may also be used to guide the applicator 16. The image data may be displayed on the display 32 as the applicator 16 is inserted into the target volume 24.

In step 104, the MRI system 12 is activated and a stable, uniform magnetic field is generated around the tissue sample (e.g., target volume 24 and the applicator 16) by the main magnet. Once the stable magnetic field is generated, the spins of a vast majority of the atoms (e.g., hydrogen nuclei) are lined up in parallel and cancel each other out and the MRI system 12 is ready to provide slide images of the target volume 24 and the field of ablation 34 to the display 32.

In step 106, the interface controller 36 signals the MRI field controller 14 to generate one or more variable magnetic fields via gradient magnets at the target volume 24 and to transmit the excitation RF pulse to the tissue surrounding the target volume 24. The excitation RF pulse precesses the atoms allowing the MRI system 12 to capture images of the tissue.

In step 108, the interface controller 36 signals the generator 28 to generate a trace RF pulse simultaneously with the MRI system 12 generating the variable magnetic fields and the excitation RF pulse. The interface controller 36 synchronizes the operation of the generator 28 and the MRI system 12 allowing for the trace signal to be transmitted to the tissue site simultaneously with the application of the variable magnetic fields and the excitation RF pulse.

The tracer pulse is of lower power than conventional RF and/or microwave ablation signal designed not to have any physical effect on the target volume 24 (e.g., desiccation). Further, in one embodiment, the tracer pulse has a frequency substantially matching the Lamour frequency of the tissue of the target volume 24, such that the tracer pulse causes the protons around the applicator 16 to absorb the energy required to make them spin, or precess, in a different direction. Since the tracer pulse is localized around the applicator 16, the affected atoms are substantially the same atoms which are affected if actual ablation pulse is applied thereto. In other words, the propagation of the tracer pulse precesses the atoms in substantially the same area as the field of ablation 34 allowing for estimation thereof. Since the tracer pulse is applied through the applicator 16 and not the RF transmitter of the MRI system 12, the resulting estimation of the field of ablation 34 is more accurate as the center of the pulse is within target volume 24.

In step 110, the MRI system 12 obtains an image of the target volume 24 based on the energy released by the precessed atoms due to the tracer pulse. Due to differing Lamour frequencies of the tissue and alteration of the local magnetic field in the tissue being examined, namely by the excitation and trace RF pulses, the MRI system 12 obtains an image of the target volume 24 with the field of ablation 34. Normal and abnormal tissue respond differently to the slight alteration, thereby releasing energy at different levels. These varied energy signals are then transferred to the images with the target volume 24 and the field of ablation 34 having different contrast from each other as well as the surrounding tissue. In one embodiment, a three-dimensional representation of the field of ablation 34 may be displayed allowing the user to rotate and zoom within the representation.

In one embodiment, multiple slices of the tissue sample may be taken to provide a better visualization of the field of ablation 34 with respect to the target volume 24. In this case, the interface controller 36 signals the generator 28 to generate the trace signal RF pulse and the MRI field controller 14 to provide corresponding magnetic field multiple times.

In step 112, once the evaluation of the image is complete, the interface controller 36 turns off the MRI system 12 and the magnetic fields generated by the magnets. The interface controller 36, thereafter signals the generator 28 that application of therapeutic energy to the tissue may commence. This prevents accidental application of energy during the MRI scanning process due to the high degree of sensitivity of the MRI system 12.

Various tissue types have different tissue properties (e.g., impedance, dielectric constant) affect the propagation of RF pulses. By applying the trace pulse to the tissue and capturing the resulting effect on MRI provides for correlation between the RF pulses and the tissue properties. The deposition of the signals into the tissue with varying properties results in a change in the intensity at gradients that with study can be correlated with tissue energy absorption characteristics.

The system 10 could be used for both RF and microwave energy delivery systems with accommodations being made to adjust the atomic spin. More specifically, when using an electrosurgical RF system, the spin can be controlled by intensifying the change to the precess spin. In a microwave ablation system, the resulting transverse magnetic field from the propagation of the current wave down the coaxial cable may be used at a lower power setting, thereby producing increased alteration to the image.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for determining field of ablation, the system comprising:
   a power source configured to generate electromagnetic energy;
   an energy applicator coupled to the power source, the energy applicator configured to be inserted into tissue and to provide electromagnetic energy to a target volume; and
   an imaging apparatus configured to generate a uniform magnetic field and at least one variable magnetic field around the tissue, wherein the imaging apparatus is further configured to obtain an image of a field of ablation within the target volume in response to a trace RF pulse supplied by the power source through the energy applicator to the target volume simultaneously with an excitation RF pulse generated by the imaging apparatus and the at least one variable magnetic field.

2. A system according to claim 1, further comprising:
   an interface controller coupled to the power source and the imaging apparatus and configured to synchronize operation thereof to provide for simultaneous application of the trace RF pulse and the excitation RF pulse.

3. A system according to claim 1, wherein the imaging apparatus is an MRI system.

4. A system according to claim 3, wherein the trace RF pulse is adapted to precess atoms of the target volume.

5. A system according to claim 1, further comprising:
   a control system coupled to the power source and the imaging apparatus and configured to automatically adjust operation thereof based on at least one of energy deposition property and at least one of magnetic field property of the energy applicator.

6. A system according to claim 5, further comprising:
   a display coupled to the control system, the display adapted to output the image of the field of ablation having a different contrast than the target volume.

7. A system according to claim 6, wherein the image of the field of ablation is a three-dimensional.

8. A system according to claim 1, wherein the energy applicator includes non-magnetic materials.

9. A method for determining field of ablation, comprising the steps of:
   providing a power source configured to generate electromagnetic energy and an energy applicator coupled to the power source, the energy applicator configured to be inserted into tissue and to provide electromagnetic energy to a target volume; and
   placing tissue into an imaging apparatus and generating a uniform magnetic field and at least one variable magnetic field around the tissue;
   supplying simultaneously a trace RF pulse through the energy applicator to the target volume and an excitation RF pulse with the at least one variable magnetic field; and
   obtaining an image of a field of ablation within the target volume in response to the trace RF pulse supplied by the power source.

10. A method according to claim 9, further comprising:
    synchronizing operation of the power source and the imaging apparatus through an interface controller coupled thereto, the interface controller configured to provide for simultaneous application of the trace RF pulse and the excitation RF pulse.

11. A method according to claim 9, wherein the step of supplying the trace RF pulse further includes the step of precessing atoms of the target volume.

12. A method according to claim 9, further comprising the steps of:
    loading at least one of energy deposition property and at least one of magnetic field property of the energy applicator into a control system coupled to the power source and the imaging apparatus; and
    automatically adjusting operation of the power source and the imaging apparatus based on at least one of energy deposition property and at least one of magnetic field property of the energy applicator.

13. A method according to claim 9, further comprising the step of outputting the image of the field of ablation having a different contrast than the target volume on a display.

14. A method according to claim 13, wherein the image of the field of ablation is a three-dimensional.

15. A system for determining field of ablation, the system comprising:
    a power source configured to generate electromagnetic energy;
    an energy applicator coupled to the power source, the energy applicator configured to be inserted into tissue and to provide electromagnetic energy to a target volume;
    an MRI system configured to generate a uniform magnetic field and at least one variable magnetic field around the tissue, wherein the MRI system obtains an image of a field of ablation within the target volume in response to a trace RF pulse supplied by the power source through the energy applicator to the target volume simultaneously with an excitation RF pulse generated by the MRI system and the at least one variable magnetic field; and
    an interface controller coupled to the power source and the MRI system and configured to synchronize operation thereof to provide for simultaneous application of the trace RF pulse and the excitation RF pulse.

16. A system according to claim 15, wherein the trace RF pulse is adapted to precess atoms of the target volume.

17. A system according to claim 15, further comprising:
    a control system coupled to the power source and the MRI system and configured to automatically adjust operation thereof based on at least one of energy deposition property and at least one of magnetic field property of the energy applicator.

18. A system according to claim 17, further comprising:
    a display coupled to the control system, the display adapted to output the image of the field of ablation having a different contrast than the target volume, wherein the image of the field of ablation is a three-dimensional.

19. A system according to claim 15, wherein the power source is selected from the group consisting of a microwave generator and an electrosurgical generator.

20. A system according to claim 15, wherein the energy applicator includes non-magnetic materials.

* * * * *